United States Patent
Rist

(10) Patent No.: US 11,697,696 B2
(45) Date of Patent: Jul. 11, 2023

(54) COMPOSITIONS FOR THE PRODUCTION OF TRANSPARENT DENTAL PARTS BY MEANS OF STEREOLITHOGRAPHY

(71) Applicant: Ivoclar Vivadent AG, Schaan (LI)

(72) Inventor: Kai Rist, Feldkirch (AT)

(73) Assignee: Ivoclar Vivadent AG, Schaan (LI)

( * ) Notice: Subject to any disclaimer, the term of this patent is extended or adjusted under 35 U.S.C. 154(b) by 557 days.

(21) Appl. No.: 16/706,102

(22) Filed: Dec. 6, 2019

(65) Prior Publication Data

US 2020/0199268 A1 Jun. 25, 2020

(30) Foreign Application Priority Data

Dec. 21, 2018 (EP) .................... 18215766

(51) Int. Cl.

| | | |
|---|---|---|
| A61C 5/00 | (2017.01) | |
| C08F 2/46 | (2006.01) | |
| C08F 2/50 | (2006.01) | |
| C08G 61/04 | (2006.01) | |
| C08F 20/36 | (2006.01) | |
| A61C 5/77 | (2017.01) | |
| A61C 13/00 | (2006.01) | |
| C08F 20/28 | (2006.01) | |
| C08K 5/00 | (2006.01) | |
| C08K 5/092 | (2006.01) | |
| C08K 5/23 | (2006.01) | |
| C08K 5/45 | (2006.01) | |
| C08K 5/57 | (2006.01) | |

(52) U.S. Cl.
CPC .............. *C08F 20/36* (2013.01); *A61C 5/77* (2017.02); *A61C 13/0013* (2013.01); *A61C 13/0019* (2013.01); *C08F 20/28* (2013.01); *C08K 5/005* (2013.01); *C08K 5/0041* (2013.01); *C08K 5/092* (2013.01); *C08K 5/23* (2013.01); *C08K 5/45* (2013.01); *C08K 5/57* (2013.01)

(58) Field of Classification Search
CPC ...... C08F 20/28; C08F 20/36; A61C 13/0019; A61C 13/0013; A61C 5/77; C08K 5/57; C08K 5/0092; C08K 5/005; C08K 5/0041; C08K 5/23; C08K 5/45; A61K 6/17; A61K 6/893; A61K 6/887; C08L 33/08; C08L 33/10
USPC .......... 433/218, 215; 522/6, 189, 184, 71, 1; 520/1
See application file for complete search history.

(56) References Cited

U.S. PATENT DOCUMENTS

| | | |
|---|---|---|
| 9,387,056 B2 | 7/2016 | Wachter et al. |
| 9,574,039 B1 | 2/2017 | Liu et al. |
| 9,944,804 B1 | 4/2018 | Liu et al. |
| 2003/0134932 A1 | 7/2003 | Lehmann et al. |
| 2003/0175660 A1 | 9/2003 | Yin et al. |
| 2008/0277814 A1 | 11/2008 | Moszner et al. |
| 2009/0131552 A1 | 5/2009 | Hsieh et al. |
| 2013/0041067 A1 | 2/2013 | Skaria et al. |
| 2017/0224591 A1 | 8/2017 | Vogel et al. |
| 2018/0057691 A1 | 3/2018 | Li et al. |
| 2018/0265527 A1 | 9/2018 | Moszner et al. |
| 2021/0361389 A1* | 11/2021 | Mac Murray ....... B29C 71/0009 |

FOREIGN PATENT DOCUMENTS

| | | |
|---|---|---|
| CN | 106189802 A | 12/2016 |
| DE | 19907957 A1 | 9/1999 |
| JP | 2001310918 A | 11/2001 |
| JP | 2019081867 * | 5/2019 |
| WO | 9700276 A1 | 1/1997 |
| WO | 2012057917 A1 | 5/2012 |
| WO | 2014172716 A1 | 10/2014 |
| WO | 2015195659 A1 | 12/2015 |
| WO | 2016071510 A1 | 5/2016 |
| WO | 2017006173 A1 | 1/2017 |
| WO | 2019023009 A1 | 1/2019 |

OTHER PUBLICATIONS

Saito et al, JP 2019-081867 Machine Translation, May 30, 2019 (Year: 2019).*
EPO, "Third Party Observations pursuant to Article 115 EPC," Third Party Observation for Application No. EP20180215766, 7 pages, May 24, 2022, Germany.
Ibrahim, Mervat S. et al., "Electron beam processed plasticized epoxy coatings for surface protection," Materials Chemistry and Physics, 130, pp. 237-242, 2011, Elsevier B.V.
Mannekutla, J.R. et al., "Rotational dynamics of UVITEX-OB in alkanes, alcohols and binary mixtures," Chemical Physics, 340, pp. 149-157, 2007, Elsevier B.V.
Gebhardt, A. "Vision Rapid Prototyping, Generative Manufacturing of Ceramic Parts—A Survey," pp. 7-13, DKG Symposium, 83 (2006) No. 13.
Gebhardt, A. "Additive Manufacturing Systems for Rapid Prototyping, Direct Tooling and Direct Manufacturing," Generative Manufacturing Processes, 3rd Edition, p. 77, Carl Hanser Verlag, Munich 2007.
Beil, A., "Production of micro-components by stereolithography," Progress Reports VDI, Series 2, No. 617, pp. 1-2, Verlag Düsseldorf, 2002.

(Continued)

*Primary Examiner* — Jessica Whiteley
(74) *Attorney, Agent, or Firm* — Ann M. Knab; Thad McMurray

(57) ABSTRACT

The present invention relates to a polymerizable composition, which comprises (a) at least one radically polymerizable compound and (b) at least one initiator for the radical polymerization, wherein the composition furthermore comprises (c) at least one UV absorber and (d) at least one optical brightener and comprises at least one radically polymerizable oligomer and at least one radically polymerizable, polyfunctional monomer as the at least one radically polymerizable compound (a).

18 Claims, No Drawings

(56) References Cited

OTHER PUBLICATIONS

Arkema, Safety Data Sheet for product CN981, May 3, 2022, Columbes, France, 8 pages.
Buruiana, T., et al., Urethane Dimethacrylate Oligomers for Dental Composite Matrix: Synthesis and Properties, Polymer Engineering and Science, 2009, pp. 1127-1135.
Novodent ETS, Safety Data Sheet for product SDB-5-1-4 Sinomer kalt N liquid, Aug. 11, 2014,10 pages.
Proclinic, Material Safety Data Sheet for Hoffmann's Ultra Violet Base, Jul. 4, 2016, Hoffmann Dental Manufaktur GmbH, 3 pages.
Mertz Dental Gmbh, Safety Data Sheet for product Combitray_LC, Jun. 24, 2017, 9 pages.
Pubchem CID 57529352, Polycaprolactone diol, Aug. 18, 2012, 15 pages.
Pubchem Cas No. 71549-84-3, Hexanedioic acid, polymer with 1,2-ethanediol and 5-isocyanato-1-isocyanatomethyl)-1,3,3-trimethylcyclohexane, 2-hydroxyethyl acrylate-blocked, Mar. 21, 2012, 1 page.
Chemical Book Cas No. 72869-86-4, Diurethane dimethacrylate, mixture of isomers, Aug. 8, 2005, 2 pages.
Merz Dental, Combitray LC Tray Materials and Combitray LC Base Trays Instructions for Use, Jun. 30, 2021, 68 pages.
Chen, H., et al., Synthesis of PCL-based Polyurethane Prepolymer for Dlp 3D Printing, IADR Abstract Archives, Jul. 25, 2018,2 pages.
Vasudeva, G., Monomer Systems for Dental Composites and Their Future: A Review, California Dental Association Journal, Jun. 2009, vol. 37, No. 6, pp. 389-398.
Orman, S., et al., Toughness Enhancers for Bone Scaffold Materials Based on Biocompatible Photopolymers, Journal of Polymer Science, Part A: Polymer Chemistry, Nov. 23, 2018, vol. 27, pp. 110-119.
Castelvetro, V., et al., UV-Curing of Acrylic Formulations by Means of Polymeric Photoinitiators with the Active 2,6-Dimethylbenzoylphosphine Oxide Moieties Pendant from a Tetramethylene Side Chain, Macromol. Chern. Phys., 2002, vol. 203, pp. 1486-1496.

\* cited by examiner

COMPOSITIONS FOR THE PRODUCTION OF TRANSPARENT DENTAL PARTS BY MEANS OF STEREOLITHOGRAPHY

CROSS-REFERENCE TO RELATED APPLICATIONS

This application claims priority to European patent application No. 18215766.9 filed on Dec. 21, 2018, the disclosure of which is incorporated herein by reference in its entirety.

TECHNICAL FIELD

The present invention relates to compositions which are suitable as dental material particularly for the production of dental parts, in particular orthodontic appliances, using additive manufacturing processes, such as e.g. stereolithography.

BACKGROUND

Malpositions can be corrected not only with conventional orthodontic processes, e.g. by means of ceramic brackets, but also with the aid of orthodontic appliances. For example, the correction of malposition with transparent plastic splints, so-called aligners, is already known from the 1940s. The transparent aligners completely cover the teeth and are to be worn for 22 hours a day and taken out only for teeth cleaning or eating and drinking. Elements for anchoring to the teeth, so-called attachments, which make it possible for the aligners to be force-fitted onto the teeth, are often also constituents of the therapy. The attachments allow controlled three-dimensional tooth movements to be carried out, such as are required for example for intrusion and extrusion or for derotation of rounded teeth such as canines or premolars. A splint, a so-called positioner, is often also recommended for optimal fine adjustment of the teeth in the last phase of the treatment with fixed braces. For the production of positioners and aligners, plaster models of both jaws are conventionally produced and each individual tooth is separated from the model. Then the teeth in wax are re-placed into the optimal position, coated with silicone and cured in a special furnace.

As with other dental materials, certain demands are also to be made on the mechanical properties of orthodontic appliances. For example, a high fracture toughness is advantageous in the case of orthodontic splints, aligners, aligner attachments, positioners bearing aligner attachments, occlusal splints, transfer splints, drilling templates, prosthesis materials, prosthetic teeth, try-ins, i.e. a prosthesis with teeth printed out in one piece and one colour for inserting and checking the fit, and denture. When in use, such parts have to withstand deformations without breaking. In general, it is true for all named materials that a high strength is advantageous at the same time. Positioners bearing aligner attachments are e.g. clipped on over the teeth, for which the positioners have to deform without breaking. As positioners and attachments have to be manufactured from the same material by reason of the process, this material must at the same time also meet the demands made on the attachment, namely to have a sufficiently high flexural modulus and a sufficiently high flexural strength.

To make use of computer-aided manufacturing processes it would furthermore be desirable if such materials could be processed using additive processes. Such additive processes, which are also often combined under the term "Rapid Prototyping" (RP), have more recently been used increasingly for the production of dental parts. By this is meant manufacturing processes in which three-dimensional models or components are produced in layers or continuously from computer-aided design data (CAD data) (A. Gebhardt, Vision of Rapid Prototyping, Ber. DGK 83 (2006) 7-12). These are processes, such as e.g. stereolithography (SL), selective laser sintering (SLS), 3D printing, fused deposition modelling (FDM), inkjet printing (IJP), 3D plotting, multijet modelling (MJM), solid freeform fabrication (SFF), laminated object manufacturing (LOM), laser powder forming (LPF), with which models, components or shaped parts can be produced cost-effectively even on a small scale (A. Gebhardt, Generative Fertigungsverfahren, 3rd Ed., Carl Hanser Verlag, Munich 2007, 77 et seq.). In the case of stereolithography a shaped part is constructed in layers from a liquid and curable monomer resin on the basis of CAD data (A. Beil, Fertigung von Mikro-Bauteilen mittels Stereolithographie, Düsseldorf 2002, VDI-Verlag 3 et seq.).

These materials thus necessarily have to be light-curing and must additionally have a low viscosity, as otherwise they cannot be processed readily in simple devices without heating and scraping.

Furthermore, high demands are to be made in particular on the optical properties of the materials. Specifically for splints, aligners, positioners and aligner attachments, as little inherent colour as possible with, at the same time, high transparency of the cured composition is particularly desirable in order to provide an orthodontic appliance which is as inconspicuous and thus as aesthetic as possible. However, this often proves to be difficult in practice, as additives, such as e.g. fillers, which are added to the composition to improve the mechanical properties, or UV blockers, which are added to the composition to better control the penetration depth of the light used for the curing and thus to improve the precision of the stereolithographic production, not infrequently have a certain, perceptible inherent colour.

SUMMARY

The object of the invention is thus to provide materials which meet the above-mentioned demands. In particular, the materials are to be light-curing and to have a low viscosity, with the result that they are to be processed in an additive manufacturing process, in particular with the aid of a stereolithographic printer. In addition, the cured materials are to be characterized in particular by a low level of inherent colour and a high transparency. Adequate mechanical properties, such as a high fracture toughness, in particular a high outer fibre strain, with at the same time a high flexural strength and a high flexural modulus, are also desirable.

DETAILED DESCRIPTION

According to the invention this object is achieved by polymerizable compositions comprising (a) at least one radically polymerizable compound and (b) at least one initiator for the radical polymerization.

The compositions according to the invention are characterized in that they furthermore contain (c) at least one UV absorber and (d) at least one optical brightener.

hydroxyethoxy)ethanol or by polymerization of 1-isocyanato-3-isocyanatomethyl-3,5,5-trimethylcyclohexane, ε-caprolactone and 2-(2-hydroxyethoxy)ethanol.

In a preferred embodiment the oligomer (a1) can be described by the following structural formula (I)

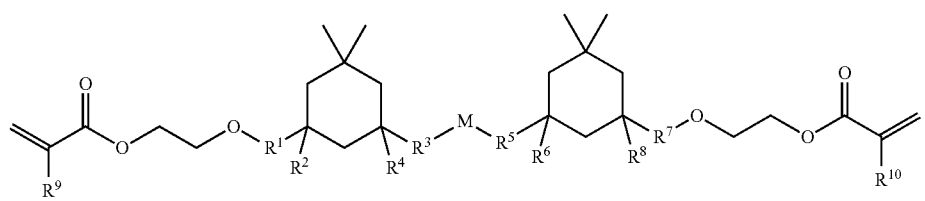

(I)

The at least one radically polymerizable compound (a) comprises a radically polymerizable oligomer and a radically polymerizable monomer which is polyfunctional.

The radically polymerizable oligomer is preferably selected from the group consisting of (i) aliphatic urethane (meth)acrylate oligomers, (ii) epoxy (meth)acrylate oligomers and (iii) polyether urethane (meth)acrylate oligomers, wherein the aliphatic urethane (meth)acrylate oligomers are preferably polyether urethane (meth)acrylate oligomers or polyester urethane (meth)acrylate oligomers. The radically polymerizable oligomer is particularly preferably selected from the group consisting of di- or tetrafunctional aliphatic urethane (meth)acrylate oligomers and difunctional epoxy (meth)acrylate oligomers.

In a first particularly preferred embodiment the compositions according to the invention are characterized in that the radically polymerizable oligomer is an oligomer (a1) which is obtainable by polymerization of 2-hydroxyethyl (meth)acrylate, 1-isocyanato-3-isocyanatomethyl-3,5,5-trimethylcyclohexane, ε-caprolactone and 2-(2-hydroxyethoxy)ethanol.

in which
$R^2$ and $R^5$ each are —C(=O)—NH— or —C(=O)—NH—$CH_2$—,
$R^3$ and $R^7$ each are —NH—C(=O)— or $CH_2$—NH—C(=O)—,
$R^2$, $R^4$, $R^6$ and $R^8$ each are H or $CH_3$,
$R^9$ and $R^{10}$ each are H or $CH_3$,
wherein,
if $R^1$ is —C(=O)—NH—, then $R^2$ is H, $R^3$ is —$CH_2$—NH—C(=O)— and $R^4$ is $CH_3$ and,
if $R^1$ is —C(=O)—NH—$CH_2$—, then $R^2$ is $CH_3$, $R^3$ is —NH—C(=O)— and $R^4$ is H,
wherein $R^1$, $R^3$, $R^5$ and $R^7$ each are inserted into the chain of structure (I) from left to right, and
M is a mid-chain segment which is obtainable by polymerization of ε-caprolactone and 2-(2-hydroxyethoxy)ethanol or by polymerization of 1-isocyanato-3-isocyanatomethyl-3,5,5-trimethylcyclohexane, ε-caprolactone and 2-(2-hydroxyethoxy)ethanol.

The oligomer (a1) can preferably be described by the following structural formula (II)

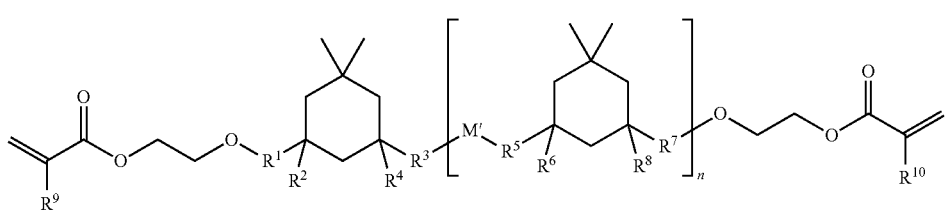

(II)

The oligomer (a1) preferably has a linear structure, wherein both chain ends in each case are formed by 2-hydroxyethyl (meth)acrylate units, with the result that 2 free acrylate or methacrylate groups per oligomer are available for the radical polymerization with the polyfunctional monomer (b) and optionally further constituents. Furthermore, it is preferred that the hydroxy groups of both terminal 2-hydroxyethyl (meth)acrylate radicals point towards the middle of the chain and each form a urethane bond with one of the two cyano groups of 1-isocyanato-3-isocyanatomethyl-3,5,5-trimethylcyclohexane. The respectively other cyano group of the 1-isocyanato-3-isocyanatomethyl-3,5,5-trimethylcyclohexane forms a urethane bond with hydroxy groups of a mid-chain segment, wherein the mid-chain segment is obtainable by polymerization of ε-caprolactone and 2-(2- in which $R^1$ to $R^{10}$ have the above meanings,

M' is a mid-chain segment which is obtainable by polymerization of ε-caprolactone and 2-(2-hydroxyethoxy)ethanol, and n is a whole number from 1 to 10, preferably 1 to 7, particularly preferably 1 to 5, such as for instance 1 to 4 or 2 to 3, and in particular 1 or 2 and quite particularly preferably 1.

In an embodiment the mid-chain segment M' in the above formula (II) is described by structural formula (III)

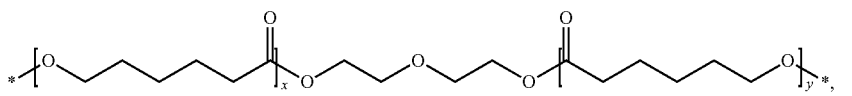

wherein x is a number from 1 to 20, preferably 1 to 15, particularly preferably 1 to 5, such as for instance 2 to 3, and y is a number from 1 to 20, preferably 1 to 15, particularly preferably 1 to 5, such as for instance 2 to 3.

It is particularly preferred that $R^9$ and $R^{10}$ each have the same meaning. In particular, $R^9$ and $R^{10}$ are both H, with the result that oligomer (a1) is selected from the group consisting of oligomers which are obtainable by polymerization of 2-hydroxyethyl acrylate, 1-isocyanato-3-isocyanatomethyl-3,5,5-trimethylcyclohexane, ε-caprolactone and 2-(2-hydroxyethoxy)ethanol.

In a second particularly preferred embodiment the oligomer is an oligomer (a2) which is obtainable by polymerization of 2-hydroxyethyl (meth)acrylate, 1-isocyanato-3-isocyanatomethyl-3,5,5-trimethylcyclohexane, adipic acid and ethylene glycol.

In a preferred embodiment the oligomer (a2) can be described by the above structural formula (I), in which $R^1$ to $R^{10}$ have the above meaning and M is a mid-chain segment which is obtainable by polymerization of adipic acid and ethylene glycol or by polymerization of 1-isocyanato-3-isocyanatomethyl-3,5,5-trimethylcyclohexane, adipic acid and ethylene glycol.

The oligomer (a2) can preferably be described by the above structural formula (II), in which $R^1$ to $R^{10}$ have the above meanings and M' is a mid-chain segment which is obtainable by polymerization of adipic acid and ethylene glycol, and n is a whole number from 1 to 10, preferably 1 to 7, particularly preferably 1 to 5, such as for instance 1 to 4 or 2 to 3, and in particular 1 or 2 and quite particularly preferably 1.

In an embodiment of oligomer (a2) the mid-chain segment M' in the above formula (II) is described by structural formula (IV)

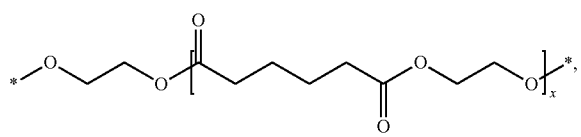

wherein x is a number from 1 to 20, preferably 1 to 15, particularly preferably 1 to 5, such as for instance 2 to 4.

It is particularly preferred that $R^9$ and $R^{10}$ each have the same meaning. In particular, $R^9$ and $R^{10}$ are both H, with the result that oligomer (a2) is selected from the group consisting of oligomers which are obtainable by polymerization of 2-hydroxyethyl acrylate, 1-isocyanato-3-isocyanatomethyl-3,5,5-trimethylcyclohexane, adipic acid and ethylene glycol.

In a third particularly preferred embodiment the oligomer is an oligomer (a3) which is obtainable by polymerization of 2-hydroxyethyl (meth)acrylate, 1-isocyanato-3-isocyanatomethyl-3,5,5-trimethylcyclohexane and tetrahydrofuran.

In a preferred embodiment the oligomer (a3) can be described by the above structural formula (I), in which $R^1$ to $R^{10}$ have the above meaning and M is a mid-chain segment which is obtainable by polymerization of tetrahydrofuran or by polymerization of 1-isocyanato-3-isocyanatomethyl-3,5,5-trimethylcyclohexane and tetrahydrofuran.

The oligomer (a3) can preferably be described by the above structural formula (II), in which $R^1$ to $R^{10}$ have the above meanings and M' is a mid-chain segment which is obtainable by polymerization of tetrahydrofuran, and n is a whole number from 1 to 10, preferably 1 to 7, particularly preferably 1 to 5, such as for instance 1 to 4 or 2 to 3, and in particular 1 or 2 and quite particularly preferably 1.

In an embodiment of oligomer (a3) the mid-chain segment M' in the above formula (II) is described by structural formula (V)

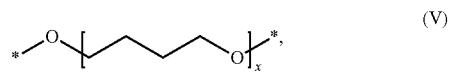

wherein x is a number from 1 to 20, preferably 1 to 15, particularly preferably 5 to 15, such as for instance 8 to 12.

It is particularly preferred that $R^9$ and $R^{10}$ each have the same meaning. In particular, $R^9$ and $R^{10}$ are both H, with the result that oligomer (a3) is selected from the group consisting of oligomers which are obtainable by polymerization of 2-hydroxyethyl acrylate, 1-isocyanato-3-isocyanatomethyl-3,5,5-trimethylcyclohexane and tetrahydrofuran. Alternatively, $R^9$ and $R^{10}$ are both $CH_3$, with the result that oligomer (a3) is selected from the group consisting of oligomers which are obtainable by polymerization of 2-hydroxyethyl methacrylate, 1-isocyanato-3-isocyanatomethyl-3,5,5-trimethylcyclohexane and tetrahydrofuran.

In a fourth particularly preferred embodiment the oligomer is an oligomer (a4) which is obtainable by polymerization of 2-hydroxyethyl (meth)acrylate, 1-isocyanato-3-isocyanatomethyl-3,5,5-trimethylcyclohexane and ethylene glycol.

In a preferred embodiment the oligomer (a4) can be described by the above structural formula (I), in which $R^1$ to $R^{10}$ have the above meaning and M is a mid-chain segment which is obtainable by polymerization of ethylene glycol or by polymerization of 1-isocyanato-3-isocyanatomethyl-3,5,5-trimethylcyclohexane and ethylene glycol.

The oligomer (a4) can preferably be described by the above structural formula (II), in which $R^1$ to $R^{10}$ have the above meanings and M' is a mid-chain segment which is obtainable by polymerization of ethylene glycol, and n is a whole number from 1 to 10, preferably 1 to 7, particularly preferably 1 to 5, such as for instance 1 to 4 or 2 to 3, and in particular 1 or 2 and quite particularly preferably 1.

In an embodiment of oligomer (a4) the mid-chain segment M' in the above formula (II) is described by structural formula (VI)

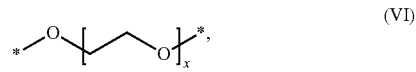

wherein x is a number from 1 to 20, preferably 1 to 15, particularly preferably 5 to 15, such as for instance 6 to 11, such as e.g. 7 to 10.

It is particularly preferred that $R^9$ and $R^{10}$ each have the same meaning. In particular, $R^9$ and $R^{10}$ are both —$CH_3$, with the result that oligomer (a4) is selected from the group consisting of oligomers which are obtainable by polymerization of 2-hydroxyethyl methacrylate, 1-isocyanato-3-isocyanatomethyl-3,5,5-trimethylcyclohexane and ethylene glycol.

In a fifth particularly preferred embodiment the oligomer is an oligomer (a5) which is obtainable by polymerization of 2-hydroxyethyl (meth)acrylate, 2,2,4-trimethylhexanediol diisocyanate and ethylene glycol.

In a preferred embodiment the oligomer (a5) can be described by the following structural formula (VII)

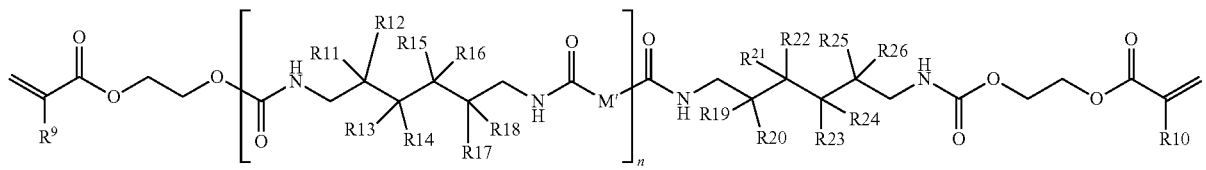

(VII)

in which
$R^9$ and $R^{10}$ have the above meaning,
$R^{11}$ to $R^{26}$ are H or $CH_3$,
wherein
  either $R^{11}$, $R^{12}$ and $R^{15}$ are $CH_3$ and $R^{13}$, $R^{14}$, $R^{16}$, $R^{17}$ and $R^{18}$ are H
  or $R^{13}$, $R^{17}$ and $R^{18}$ are $CH_3$ and $R^{11}$, $R^{12}$, $R^{14}$, $R^{15}$ and $R^{16}$ are H, and
  either $R^{19}$, $R^{20}$ and $R^{23}$ are $CH_3$ and $R^{21}$, $R^{22}$, $R^{24}$, $R^{25}$ and $R^{26}$ are H
  or $R^{21}$, $R^{25}$ and $R^{26}$ are $CH_3$ and $R^{19}$, $R^{20}$, $R^{22}$, $R^{23}$ and $R^{24}$ are H,
M' is a mid-chain segment which is obtainable by polymerization of ethylene glycol, and
n is a whole number from 1 to 10, preferably 1 to 7, particularly preferably 1 to 5, such as for instance 1 to 4 or 2 to 3, and in particular 1 or 2.

In an embodiment of oligomer (a5) the mid-chain segment M' in the above formula (VII) is described by structural formula (VIII)

(VIII)

wherein x is a number from 1 to 20, preferably 1 to 15, particularly preferably 5 to 15, such as for instance 6 to 11, such as e.g. 6 to 9.

It is particularly preferred that $R^9$ and $R^{10}$ each have the same meaning. In particular, $R^9$ and $R^{10}$ are both —$CH_3$, with the result that oligomer (a5) is selected from the group consisting of oligomers which are obtainable by polymerization of 2-hydroxyethyl methacrylate, 2,2,4-trimethylhexanediol diisocyanate and ethylene glycol.

In a sixth particularly preferred embodiment the oligomer is an oligomer (a6) which is obtainable by polymerization of 2-hydroxyethyl (meth)acrylate, 2,2,4-trimethylhexanediol diisocyanate and tetrahydrofuran.

In a preferred embodiment the oligomer (a6) can be described by the above structural formula (VII), in which $R^9$ to $R^{26}$ have the above meaning, M' is a mid-chain segment which is obtainable by polymerization of tetrahydrofuran, and n is a whole number from 1 to 10, preferably 1 to 7, particularly preferably 1 to 5, such as for instance 1 to 4 or 2 to 3, and in particular 1 or 2.

In an embodiment of oligomer (a6) the mid-chain segment M' in the above formula (VII) is described by structural formula (IX)

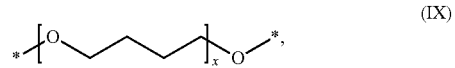

(IX)

wherein x is a number from 1 to 20, preferably 1 to 15, particularly preferably 5 to 15, such as for instance 7 to 12, such as e.g. 8 to 11.

It is particularly preferred that $R^9$ and $R^{10}$ each have the same meaning. In particular, $R^9$ and $R^{10}$ are both —$CH_3$, with the result that oligomer (a6) is selected from the group consisting of oligomers which are obtainable by polymerization of 2-hydroxyethyl methacrylate, 2,2,4-trimethylhexanediol diisocyanate and tetrahydrofuran.

In a seventh particularly preferred embodiment the oligomer is an oligomer (a7) which is an aliphatic tetrafunctional urethane methacrylate oligomer with a molar mass of from approximately 7000 to 9000 g/mol, in particular approximately 8000 g/mol, measured by means of GPC, and is preferably present in the form of a mixture with triethylene glycol dimethacrylate, wherein the mixture preferably comprises 80 to 95 wt.-%, in particular approximately 90 wt.-%, of oligomer (a7). For example, oligomer (a7) is Miramer U3400 NT, obtainable from Miwon Specialty Chemical Co., Ltd.

In an eighth particularly preferred embodiment the oligomer (a) is an oligomer (a8) which is a difunctional epoxy acrylate oligomer with a molar mass of from approximately 6000 to 7000 g/mol, such as for instance 6600 g/mol, such as e.g. Photocryl E207, obtainable from Miwon Specialty Chemical Co., Ltd.

The composition according to the invention quite particularly preferably comprises the above-described oligomer (a1) as oligomer.

The radically polymerizable oligomer preferably has a molar mass (expressed as the number-average molecular weight Mn, which can be calculated, in particular in the case of polyester urethane oligomers, via the hydroxyl value of the polyester diol used in the synthesis as well as the molar masses of the isocyanate and (meth)acrylate used for the synthesis) of more than 500 g/mol, in particular 500 to 10,000 g/mol, such as e.g. 500 to 8000 g/mol or 1000 to 7000 g/mol or 1000 to 5000 g/mol, particularly preferably 500 to 3000 g/mol, such as e.g. 1200 to 2500 g/mol. Furthermore, it is preferred that the radically polymerizable oligomer has a viscosity of from 5 to 150, preferably 10 to 50, in particular 20 to 25 Pas, measured by means of rotational viscometry at 50° C.

The radically polymerizable oligomer is present, relative to the total weight of the composition, preferably in an amount of from 25 to 60 wt.-%, in particular 30 to 55 wt.-%, such as e.g. 32 to 50 wt.-%. For the case where the composition according to the invention contains a filler (e), as described below, the quantity of radically polymerizable oligomer is preferably 38 to 42 wt.-%. For the case where the composition according to the invention does not contain a filler, the quantity of radically polymerizable oligomer is preferably 40 to 55 wt.-%, in particular 45 to 50 wt.-%.

It has surprisingly been found that the use of an above-described oligomer in combination with a polyfunctional monomer and an initiator (b) yields compositions which are light-curing and low-viscosity, with the result that they can be processed using stereolithographic processes, and the cured compositions have a high transparency and little inherent colour, as well as a high fracture toughness, in particular a high outer fibre strain, with at the same time a high flexural strength and a high flexural modulus. The compositions according to the invention are thus outstandingly suitable as dental material, in particular for the production of orthodontic appliances such as aligners, aligner attachments and positioners.

In addition to the oligomer, the compositions according to the invention preferably also contain a polyfunctional monomer which is radically polymerizable as radically polymerizable compound. By polyfunctional monomers is meant compounds with two or more, preferably 2 to 6, such as e.g. 2 to 3 or 2 to 4, radically polymerizable groups. The polyfunctional monomer preferably has (meth)acrylates and/or (meth)acrylamides as radically polymerizable groups.

Particularly suitable polyfunctional monomers are (meth)acrylic acid derivatives selected from the group consisting of bisphenol A di(meth)acrylate, bis-G(M)A (an addition product of (meth)acrylic acid and bisphenol A diglycidyl ether), ethoxylated or propoxylated bisphenol A di(meth)acrylate, such as e.g. bisphenol A di(meth)acrylate with 3 (SR-348c=methacrylate; SR-349=acrylate, from Sartomer) or 2 (SR-348L=methacrylate, from Sartomer) ethoxy groups, 2,2-bis[4-(2-(meth)acryloxypropoxy)phenyl]propane, UD(M)A (an addition product of 2-hydroxyethyl (meth)acrylate and 2,2,4- or 2,4,4-trimethylhexamethylene-1,6-diisocyanate), di-, tri-, tetra-, penta-, hexa- or heptaethylene glycol di(meth)acrylate, di-, tri-, tetra-, penta-, hexa- or heptapropylene glycol di(meth)acrylate, trimethylolpropane tri(meth)acrylate, ethoxylated or propoxylated trimethylolpropane tri(meth)acrylate, e.g. trimethylolpropane triacrylate propoxylated 3 times (Sartomer SR-492) and tripropylene glycol diacrylate, pentaerythritol tetra(meth)acrylate, as well as glycerol di- and tri(meth)acrylate, 1,4-butanediol di(meth)acrylate, 1,10-decanediol di(meth)acrylate ($D_3MA$), 1,12-dodecanediol di(meth)acrylate, polyether (meth)acrylates, polyester (meth)acrylates, epoxy (meth)acrylates, urethane (meth)acrylates, tricyclodecane dimethanol di(meth)acrylate, N,N-dimethacrylamide, crosslinking pyrrolidones such as 1,6-bis-(3-vinyl-2-pyrrolidonyl) hexane, bisacrylamides such as methylene or ethylene bisacrylamide and bis(meth)acrylamides such as N,N'-diethyl-1,3-bis(acrylamido)propane, 1,3-bis(methacrylamido) propane, 1,4-bis(acrylamido)butane or 1,4-bis(acryloyl)piperazine.

Di- and trifunctional acrylates and methacrylates with a molecular weight of <1000 g/mol, such as e.g. glycerol 1,3-dimethacrylate-2-acetate, aliphatic urethane diacrylates, phthalic acid HEA ester (Photomer 4173), pyromellitic acid di-di-HEA ester (HEA=2-hydroxyethyl acrylate), bis-G (M)A (an addition product of (meth)acrylic acid and bisphenol A diglycidyl ether), 2,2-bis[4-(2-(meth)acryloxypropoxy)phenyl]propane, UD(M)A, triethylene glycol di(meth)acrylate (TEGD(M)A), 2-phenoxyethyl (meth)acrylate (acrylate SR339C from Sartomer/Arkema), tricyclodecane dimethanol dimethacrylate (CAS 43048-08-4) and FLKP crosslinker, i.e. the reaction product of 1,3-phenylenebis(propane-2,2-diylcarbamoyloxyethane-2,1-diyl) bis(2-methylacrylate) (CAS 178884-91-1), 2-{[(2-{-[2-methacryloyloxy)ethoxy]carbonyl}amino)propan-2-yl] phenyl}propan -2-yl)carbamoyl]oxy}propyl methacrylate (CAS 1219495-43-8) and 1,3-phenylenebis(propane-2,2-diylcarbamoyloxypropane-2,1-diyl) bis(2-methylacrylate) (CAS 138393-21-2), are particularly preferred. These monomers are characterized by a high reactivity, a high double bond conversion, good mechanical properties, low polymerization shrinkage and a relatively low viscosity. Compositions comprising UDMA, TEGDMA, bis-GMA, 2-phenoxyethyl acrylate (SR339C, from Sartomer/Arkema), glycerol 1,3-dimethacrylate-2-acetate or a mixture thereof, in particular a mixture of UDMA, TEGDMA and 2-phenoxyethyl acrylate or preferably a mixture of UDMA, TEGDMA and bis-GMA or a mixture of UDMA and TEGDMA or a mixture of UDMA, TEGDMA, bis-GMA and glycerol 1,3-dimethacrylate-2-acetate, as polyfunctional monomer are quite particularly preferred.

The use of polyfunctional monomers having polar groups, such as e.g. OH groups, amide groups, urethane groups and/or urea groups, has proved to be particularly advantageous. It is assumed that such polar groups can lead to the formation of intermolecular hydrogen bridge bonds, whereby the fracture toughness of the cured composition is not reduced too strongly.

The radically polymerizable polyfunctional monomer or a mixture thereof is present, relative to the total weight of the composition according to the invention, preferably in an amount of from 30 to 65 wt.-%, in particular 30 to 60 wt.-%, such as e.g. 35 to 50 wt.-%, particularly preferably 38 to 45 wt.-%, in particular 38 to 41 wt.-%.

In addition to the radically polymerizable oligomer and the radically polymerizable, polyfunctional monomer, the composition according to the invention can furthermore optionally contain one or more monofunctional monomers. Particularly suitable monofunctional monomers are monofunctional (meth)acrylates, such as e.g. methyl, ethyl, 2-hydroxyethyl, butyl, benzyl, tetrahydrofurfuryl or isobornyl (meth)acrylate, p-cumylphenoxyethylene glycol methacrylate (CMP-1E) and dicyclopentanyl methacrylate (CAS No. 34759-34-7). The composition according to the invention particularly preferably contains dicyclopentanyl methacrylate and/or p-cumylphenoxyethylene glycol methacrylate (CMP-1E) as monofunctional monomer.

The monofunctional monomer is preferably present, relative to the total weight of the composition according to the invention, in an amount of from 0 to 15 wt.-%, particularly preferably 0 to 10 wt.-%, in particular 5 to 10 wt.-% or 7 to 9 wt.-%.

Particular properties of the materials before and after curing can be influenced by a targeted combination of the monomers. In the case of mixtures of monofunctional and difunctional monomers, for example, the viscosity and reactivity decrease as the monofunctional monomers content decreases. Mixtures of difunctional and trifunctional monomers have a higher reactivity, wherein the reactivity increases as the trifunctional monomers content increases. However, the trifunctional monomers content also brings about a greater brittleness of the cured composition. Reactivity and viscosity of the uncured composition as well as the polymerization shrinkage are moreover determined by the molar mass of the monomers, wherein as the molar mass increases the polymerization shrinkage decreases, while the viscosity rises.

For combinations of oligomers and polyfunctional monomers or combinations of oligomers, polyfunctional monomers and monofunctional monomers, on the other hand, no general principles are known. Instead, it has surprisingly been found by the inventors of the present invention that the use of the specific oligomers described above, in particular oligomer (a1), in combination with polyfunctional monomers, in particular in combination with a mixture of UDMA, TEGDMA and bis-GMA as polyfunctional monomer, and optionally dicyclopentanyl methacrylate as monofunctional monomer, leads to materials with particularly favourable properties, namely to compositions which can be processed with simple stereolithographic processes, which after curing have a high fracture toughness, in particular a high outer fibre strain, with at the same time a high flexural strength and a high flexural modulus and which are additionally characterized by a low level of inherent colour and a high transparency.

Suitable photoinitiators (b) for initiating the radical photopolymerization are benzophenone, benzoin as well as derivatives thereof or α-diketones or derivatives thereof, such as 9,10-phenanthrenequinone, 1-phenylpropane-1,2-dione, diacetyl or 4,4'-dichlorobenzil. Preferably camphorquinone (CQ) and 2,2-dimethoxy-2-phenylacetophenone and quite particularly preferably α-diketones in combination with amines, as reducing agent, are used, such as e.g. 4-(dimethylamino)benzoic acid ester (EDMAB), N,N-dimethylaminoethyl methacrylate, N,N-dimethyl-sym.-xylidine or triethanolamine. Diethylthioxanthene (DETX, CAS 82799-44-8) and isopropylthioxanthone (ITX, CAS 75081-21-9), both in each case preferably in combination with ethyl 4-(dimethylamino)benzoate (EMBO, CAS No. 10287-53-3), are further preferred. [1-/4-Phenylsulfanylbenzoyl)heptylideneamino] benzoate (Irgacure OXE 01) and [1[9-ethyl-6-(2-methylbenzoyl)carbazol-3-yl]ethylideneamino] acetate (Irgacure OXE 02) are also preferred.

Particularly preferred photoinitiators are furthermore Norrish type I photoinitiators, above all monoacyl- or bisacylphosphine oxides, such as e.g. diphenyl-(2,4,6-trimethylbenzoyl)phenylphosphine oxide (CAS No. 75980-60-8), and in particular monoacyltrialkyl- or diacyldialkyl- or tetraacylgermanium compounds, such as e.g. benzoyltrimethylgermanium, dibenzoyldiethylgermanium, bis(4-methoxybenzoyl)diethylgermanium (MBDEGe), tetrakis(4-ethoxybenzoyl)germanium or tetrakis(4-propoxybenzoyl) germanium, or acyl tin compounds, such as monoacyl stannanes, diacyl stannanes, triacyl stannanes or tetraacyl stannanes, such as e.g. benzoyl triphenyltin. Further preferred acyl germanium compounds are described in EP 3 150 641 A1 and further preferred acyl tin compounds are described in EP 3 293 215 A1. Mixtures of the different photoinitiators can also be used advantageously, such as e.g. bis(4-methoxybenzoyl)diethylgermanium in combination with camphorquinone and 4-dimethylaminobenzoic acid ethyl ester.

Camphorquinone (CAS No. 10373-78-1) in combination with ethyl 4-(dimethylamino)benzoate (EMBO, CAS No. 10287-53-3) as well as phenylbis(2,4,6-trimethylbenzoyl) phosphine oxide (Irgacure 819, CAS 162881-26-7), diphenyl(2,4,6-trimethylbenzoyl)phenylphosphine oxide (TPO, CAS No. 75980-60-8), 2-benzyl-2-(dimethylamino)-4'-morpholinobutyrophenone (Irgacure 369, CAS No. 119313-12-1), 1-butanone-2-(dimethylamino)-2-(4-methylphenyl) methyl-1-4-(4-morpholinyl)phenyl (Irgacure 379, CAS No. 119344-86-4) and quite particularly bis(4-methoxybenzoyl) diethylgermanium (MBDEGe; Ivocerin), tetrakis(4-ethoxybenzoyl)germanium or tetrakis(4-propoxybenzoyl)germanium are quite particularly preferred. In particular, the preferred photoinitiators are those which either have only very little inherent colour or lose their colour when irradiated with light, e.g. in a stereolithographic printing process or in a post-treatment process.

The composition according to the invention contains the photoinitiator (b) preferably in a quantity of from 0.1 to 3.0 wt.-%, in particular 0.5 to 2 wt.-%, particularly preferably 0.7 to 1.5 wt.-%, such as e.g. 0.8 to 1.3 wt.-%.

In addition to the above-mentioned components, the compositions according to the invention furthermore comprise at least one UV absorber (c).

The UV absorber serves to reduce the penetration depth of the light, and thus the polymerization depth, during the light-induced curing of the composition according to the invention. This proves to be advantageous in particular in the case of stereolithographic uses, as only thin layers are to be cured in stereolithography. The use of a UV absorber can thus improve the precision in stereolithographic processes. In addition, UV absorbers can also be added as colorant for aesthetic purposes.

As UV absorber or so-called colorant, organic dyes and pigments are preferred, in particular azo dyes, carbonyl dyes, cyanine dyes, azomethines and methines, phthalocyanines and dioxazines. Dyes which are soluble in the materials, in particular azo dyes, are particularly preferred. Moreover, inorganic and in particular organic pigments which can be dispersed well in the materials are suitable as colorant. Azo pigments and non-azo pigments are preferred. For example, UV absorbers based on benzotriazole, benzophenone or triazines are particularly suitable. Preferred UV absorbers are, for example, 2,2'-methylenebis[6-(2H-benzotriazol-2-yl)-4-(1,1,3,3-tetramethylbutyl)phenol] (CAS No. 103597-45-1), 2,2',4,4'-tetrahydroxybenzophenone (CAS No. 131-55-5), 2-tert-butyl-6-(5-chloro-2H-benzotriazol-2-yl)-4-methylphenol (bumetrizole; CAS No. 3896-11-5), 2,2'-benzene-1,4-diylbis(4h-3,1-benzoxazin-4-one) (CAS No. 18600-59-4), 2-(4,6-bis-(2,4-dimethylphenyl)-1,3,5-triazin-2-yl)-5-(octyloxy)phenol (CAS No. 2725-22-6), 2-(2-hydroxy-5-methylphenyl)benzotriazole (CAS No. 2440-22-4), 2-(2-hydroxyphenyl)benzotriazole, 2-(2H-benzotriazol-2-yl)-6-dodecyl-4-methylphenol (CAS No. 23328-53-2), 2-(2'-hydroxy-3',5'-di-t-butylphenyl)-5-chlorobenzotriazole (CAS No. 3864-99-1), 2,2'-dihydroxy-4-methoxybenzophenone (CAS No. 131-53-3) and 2,2'-dihydroxy-4,4'-dimethoxybenzophenone (CAS No. 131-54-4).

So-called Hindered Amine Light Stabilizers such as bis (1,2,2,6,6-pentamethyl-4-piperidyl) sebacate (CAS No. 41556-26-7), methyl-1,2,2,6,6-pentamethyl-4-piperidyl sebacate (CAS No. 82919-37-7), bis(1-octyloxy-2,2,6,6-tetramethyl-4-piperidyl) sebacate (CAS No. 129757-67-1) and bis(1,2,2,6,6-pentamethyl-4-piperidyl) [[3,5-bis (1,1-dimethylethyl)-4-hydroxyphenyl]methyl]butylmalonate (CAS No. 63843-89-0) are also suitable. Examples of further suitable so-called Hindered Amine Light Stabilizers include compounds with CAS No. 52829-07-9, CAS No. 124172-53-8, CAS No. 65447-77-0, CAS No. 167078-06-0, CAS No. 106990-43-6, CAS No. 70624-18-9, CAS No. 82451-48-7, CAS No. 136504-96-6 or CAS No. 191743-75-6.

The composition according to the invention particularly preferably comprises bumetrizole as UV absorber. In an alternative preferred embodiment the UV absorber is 2,2',4,4'-tetrahydroxybenzophenone.

The composition preferably contains at least one UV absorber, which has an absorption maximum which corresponds to the wavelength of the light used for the curing. UV absorbers with an absorption maximum below 400 nm or in the range of from 350 to 550 nm, preferably 380 to 480 nm, are very advantageous.

Moreover, in addition to a UV absorber (c), the composition according to the invention furthermore comprises an optical brightener (d). The optical brightener (d) is preferably a fluorescent compound. In particular, the optical brightener (d) preferably absorbs light in the UV range, i.e. below 400 nm. It is thereby possible to reduce the penetration depth of the light, and thus the polymerization depth, and increase the precision in the case of stereolithographic uses. Moreover, the optical brightener is preferably capable of emitting light absorbed in the UV range as light with a wavelength of from preferably 400 to 450 nm. Thus, the optical brightener can furthermore lead to an increase in the reactivity of the composition, as the brightener re-emits the absorbed light as blue light because of its fluorescence, and thus provides additional light power for photoinitiation.

The optical brightener (d) is preferably selected from the group consisting of 2,5-bis(5-tert-butyl-benzoxazol-2-yl)thiophene (CAS No. 7128-64-5) fluorescent agents in the form of terephthalic acid derivatives, such as e.g. terephthalic acid derivatives which are obtainable e.g. under the name Lumilux blue LZ from Honeywell Specialty Chemicals Seelze, Germany, or diethyl 2,5-dihydroxyterephthalate (CAS No. 5870-38-2).

The UV absorber (c) is preferably present, relative to the total weight of the composition according to the invention, in an amount of from 0 to 2.0 wt.-%, particularly preferably 0.0001 to 0.5 wt.-%. In the case of bumetrizole as UV absorber, the amount thereof is preferably 0.01 to 0.2 wt.-%, particularly preferably 0.02 to 0.15 wt.-%. In the case of 2,2',4,4'-tetrahydroxybenzophenone as UV absorber, the amount is preferably smaller, and in particular is 0.01 to 0.07 wt.-%. The amount of UV absorber (c) is smaller in the case of compositions which contain one or more fillers than in the case of unfilled compositions.

Furthermore, it is preferred that the optical brightener (d) is present, relative to the total weight of the composition according to the invention, in an amount of from 0.001 to 0.1 wt.-%, preferably 0.002 to 0.05 wt.-%, particularly preferably 0.005 to 0.02 wt.-%.

Moreover, it is preferred that the ratio by weight of UV absorber (c) to optical brightener (d) is from 2:1 to 50:1, preferably from 2:1 to 30:1, particularly preferably from 2:1 to 5:1 or from 10:1 to 25:1.

It has been found that such combinations of UV absorber (c) and optical brightener (d) after curing of the composition according to the invention lead to particularly transparent materials without visually perceptible inherent colour. After the curing, the composition according to the invention is particularly preferably characterized by a transparency of 80% or more, in particular 90% or more, measured as luminosity using a Minolta CM-5 spectrophotometer in transmission mode against a D65 light source as parameter Y in the Yxy colour space on 2-mm-thick highly polished test pieces.

Particularly ideal results with particularly high transparency and particularly little inherent colour can be achieved if the composition according to the invention contains 2,2',4,4'-tetrahydroxybenzophenone or bumetrizole as UV absorber (c) and 2,5-bis(5-tert-butyl-benzoxazol-2-yl)thiophene as optical brightener (d). In particular, the composition according to the invention contains 2,2',4,4'-tetrahydroxybenzophenone and 2,5-bis(5-tert-butyl-benzoxazol-2-yl)thiophene in a ratio by weight of from 2:1 to 10:1, preferably from 2:1 to 5:1, or bumetrizole and 2,5-bis(5-tert-butyl-benzoxazol-2-yl)thiophene in a ratio by weight of from 5:1 to 30:1, preferably from 10:1 to 20:1.

The compositions according to the invention can moreover comprise particulate filler (e). In general, inorganic and/or organic particles can be used as fillers. The filler or fillers preferably has/have a particle size of less than 25 μm, preferably less than 10 μm and particularly preferably less than 5 μm. All particle sizes herein are, unless otherwise indicated, D50 values, i.e. 50 vol.-% of the particles have a diameter which is smaller than the value indicated. Fillers serve primarily to adjust the viscosity of the curable composition as well as the mechanical and/or optical properties of the cured materials. Furthermore, it is preferred that the maximum particle size is smaller than the thickness of the layers generated by stereolithography. Particles with a maximum size of 25 μm, preferably at most 15 μm, are preferred.

The surface of the fillers can be modified, for example in order to improve the dispersibility of the fillers in the organic matrix of the composition according to the invention. Those compounds which are chemically bonded, i.e. by ionic or covalent bonds, to the surface of the fillers are preferably used for the surface modification. Compounds which contain either acid groups, preferably carboxylic acid groups, phosphonic acid groups, hydrogen phosphate groups or acidic phosphoric acid ester groups, or silyl groups, preferably alkoxysilyl groups, are preferred. The particle surface can be partially or preferably completely covered with the modifier. The modifiers used according to the invention are monomeric compounds. Linear carboxylic acids, such as e.g. formic acid, acetic acid, propionic acid, octanoic acid, isobutyric acid, isovaleric acid, pivalic acid, or phosphonic acids, e.g. such as methyl-, ethyl-, propyl-, butyl-, hexyl-, octyl- or phenylphosphonic acid, are particularly suitable as surface modifier. Silanes such as propyltrimethoxysilane, phenyltrimethoxysilane, hexyltrimethoxysilane, octyltrimethoxysilane, trimethylchlorosilane, trimethylbromosilane, trimethylmethoxysilane and hexamethyldisilazane are preferred as compounds containing silyl groups. Quite particularly preferred surface modifiers are acidic phosphoric acid esters, such as e.g. dimethyl, diethyl, dipropyl, dibutyl, dipentyl, dihexyl, dioctyl or di(2-ethylhexyl) phosphate. The surface modifiers can also have radically polymerizable groups, for example (meth)acrylate groups, which react with the component (a) and are thus incorporated into the polymer network.

Preferred fillers are particulate waxes, in particular carnauba wax, preferably with a particle size of from 1 to 10 μm, crosslinked polymethyl methacrylate (PMMA) particles, preferably with a particle size of from 500 nm to 10 μm, as well as polyamide 12 particles, preferably with a particle size of from 5 to 10 μm. Quite particularly preferred fillers are glass fillers, in particular glass fillers which before any surface modification have a particle size of from 0.2 to 2.0 µm, preferably 0.5 to 1.5 µm. Likewise particularly preferably, the composition contains a so-called prepolymer filler or isofiller, i.e. a ground composite material which preferably has a broad particle-size distribution, e.g. with particle sizes of from 0.05 to 20 µm, in particular approximately 0.1 to approximately 10 µm. In an embodiment, the prepolymer filler or isofiller preferably has a bimodal particle-size distribution, wherein preferably more than 50%, in particular more than 70% and particularly preferably more than 80% of the filler particles have a particle size of from 1 to 15 µm, measured by means of laser diffraction with a CILAS 1064 particle-size measuring device in water with Teepol dispersant (Teepol L from BDH Laboratory SUPPLIES; Poole BH15 1TD, England) accompanied by ultrasonic dispersion. The prepolymer filler or isofiller is preferably surface-modified, in particular silanized. In the case of surface-modified prepolymer fillers or isofillers, the above-named particle sizes relate to the particle sizes before the surface modification, i.e. of the fillers before e.g. silanization.

In a preferred embodiment, the composition according to the invention comprises a mixture of two or more fillers, in particular of two or more fillers with different particle sizes. It has been found that the use of such filler mixtures does not increase the viscosity of the composition excessively and the compositions can therefore furthermore be processed with additive processes, such as e.g. using stereolithography. A mixture of a silanized glass filler (i) with a particle size of approximately 0.7 µm (before the silanization), a silanized glass filler (ii) with a particle size of approximately 1.0 µm (before the silanization) and a prepolymer filler (iii) with a broad particle-size distribution of from approximately 0.1 to approximately 10 µm is particularly preferred. Furthermore, it is quite particularly preferred that the composition according to the invention contains, relative to its total weight, 2.0 to 4.0 wt.-%, in particular 2.5 to 3.5 wt.-%, of glass filler (i), 0.5 to 2.0 wt.-%, in particular 1.0 to 1.6 wt.-%, of glass filler (ii) and 4.0 to 6.0 wt.-%, in particular 4.5 to 5.5 wt.-%, of prepolymer filler (iii).

In an alternative preferred embodiment, the composition according to the invention is free of fillers (e).

In general, the composition according to the invention preferably contains 0 to 15 vol.-% of filler(s) (e). This preferably corresponds to an amount of from 0 to 40 wt.-%, in particular 0 to 20 wt.-% and particularly preferably 0 wt.-% or 6.0 to 20.0 wt.-%, such as e.g. 8.0 to 15.0 wt.-% or 8.0 to 10.0 wt.-%, of filler (e), relative to the total weight of the composition according to the invention.

In case the composition according to the invention comprises one or more fillers (e), the composition preferably furthermore also comprises a thixotropic additive (f). This additive (f) represents a thickening agent and serves to prevent a sedimentation of the fillers in the composition. In order not to increase the viscosity of the composition too strongly, the composition preferably contains only small amounts of thixotropic additive (f), such as e.g. 0 to 3.0 wt.-%, in particular 0 to 2.0 wt.-%, particularly preferably 0.1 to 2.0 wt.-% or 0.5 to 2.0 wt.-%, relative to the total weight of the composition. Preferred thixotropic additives (f) are in particular selected from the group consisting of $SiO_2$, highly disperse $SiO_2$, i.e. $SiO_2$ with a small primary particle size and a large surface area, polymers, block copolymers and sheet silicates.

In addition to the above-mentioned components, the compositions according to the invention can comprise one or more further additives.

For example, the compositions can contain one or more polymerization inhibitors. The polymerization inhibitor or inhibitors serves/serve as stabilizer to prevent a spontaneous polyreaction. The inhibitors or stabilizers improve the storage stability of the compositions and in addition prevent an uncontrolled polyreaction in the stereolithography tank. The inhibitors are preferably added in such an amount that the compositions are storage-stable over a period of approx. 2-3 years. The inhibitors are particularly preferably used in an amount of from 0.001 to 1.0 wt.-%, quite particularly preferably 0.001 to 0.20 wt.-%, in each case relative to the total mass of the composition.

It is preferred to use so-called aerobic inhibitors like phenols, such as hydroquinone monomethyl ether (MEHQ) or 2,6-di-tert.-butyl-4-methylphenol (BHT), which are effectively active only in the presence of oxygen and are preferably used in a concentration range of 100-2000 ppmw. Suitable anaerobic inhibitors are phenothiazine, 2,2,6,6-tetramethylpiperidine-1-oxyl radical (TEMPO), iodine and copper(I) iodide. These are already active in low concentrations of preferably 10-200 ppmw even in the absence of oxygen. Polymerization does not take place until these additives are consumed. It is advantageous here to use a mixture of aerobic and anaerobic inhibitors.

Aerobic inhibitors are preferably used in an amount of from 0.001 to 0.50 wt.-% and anaerobic inhibitors in an amount of from 0.001 to 0.02 wt.-%, in each case relative to the total mass of the composition. Preferred mixtures contain 0.005-0.10 wt.-% of aerobic inhibitors and 0.001-0.02 wt.-% of anaerobic inhibitors, likewise relative to the total mass of the composition.

The compositions according to the invention therefore preferably have the following composition:
(a') 25 to 60 wt.-%, in particular 30 to 55 wt.-%, such as e.g. 32 to 50 wt.-%, particularly preferably 38 to 42 wt.-%, oligomer, preferably oligomer (a1),
(a") 30 to 65 wt.-%, in particular 30 to 60 wt.-%, more preferably 35 to 50 wt.-%, particularly preferably 38 to 45 wt.-%, in particular 38 to 41 wt.-%, polyfunctional monomer,
(b) 0.1 to 3.0 wt.-%, in particular 0.5 to 2 wt.-%, particularly preferably 0.7 to 1.5 wt.-%, in particular 0.8 to 1.3 wt.-%, photoinitiator,
(a''') 0 to 15 wt.-%, particularly preferably 0 to 10 wt.-%, in particular 5 to 10 wt.-% or 7 to 9 wt.-%, monofunctional monomer,
(c) 0.0001 to 2.0 wt.-%, particularly preferably 0.0001 to 0.5 wt.-%, UV absorber,
(d) 0.001 to 0.1 wt.-%, particularly preferably 0.002 to 0.05 wt.-%, optical brightener,
(e) 0 to 40 wt.-%, in particular 0 to 20 wt.-%, particularly preferably 0 wt.-% or 6.0 to 20.0 wt.-%, in particular 8.0 to 15.0 wt.-% or 8.0 to 10.0 wt.-%, filler and
(f) 0 to 3.0 wt.-%, in particular 0 to 2.0 wt.-%, particularly preferably 0.1 to 2.0 wt.-% or 0.5 to 2.0 wt.-%, thixotropic additive,
in each case relative to the total weight of the composition.
A quite particularly preferred composition comprises:
(a') 40 to 60 wt.-%, in particular 45 to 55 wt.-%, such as e.g. 48 to 52 wt.-%, oligomer, preferably oligomer (a1),
(a") 40 to 60 wt.-%, in particular 45 to 55 wt.-%, particularly preferably 46 to 52 wt.-%, polyfunctional monomer, wherein the polyfunctional monomer is preferably a mixture of UDMA, TEGDMA and bis-GMA,
(b) 0.5 to 2 wt.-%, particularly preferably 0.7 to 1.5 wt.-%, in particular 0.8 to 1.3 wt.-%, photoinitiator, (a''') 0 to 10 wt.-%, particularly preferably 0 to 5 wt.-%, in particular 0 wt.-%, monofunctional monomer,
(c) 0.0001 to 2.0 wt.-%, particularly preferably 0.01 to 0.5 wt.-%, particularly preferably 0.05 to 0.3 wt.-%, UV absorber,
(d) 0.001 to 0.1 wt.-%, particularly preferably 0.002 to 0.05 wt.-%, optical brightener,
(e) 0 to 40 wt.-%, in particular 0 to 20 wt.-%, particularly preferably 0 wt.-%, filler and
(f) 0 to 3.0 wt.-%, in particular 0 to 2.0 wt.-%, particularly preferably 0 wt.-%, thixotropic additive,
in each case relative to the total weight of the composition, wherein the mixture of UDMA, TEGDMA and bis-GMA preferably comprises, relative to the total weight of the composition,
(a''1) 10 to 20 wt.-%, particularly preferably 12 to 18 wt.-%, UDMA,
(a''2) 20 to 35 wt.-%, particularly preferably 25 to 33 wt.-%, TEGDMA and
(a''3) 3 to 20 wt.-%, particularly preferably 3 to 10 wt.-%, bis-GMA.

In a further quite preferred embodiment the composition comprises:
(a') 37 to 55 wt.-%, in particular 39 to 47 wt.-%, such as e.g. 43 to 46 wt.-%, oligomer, preferably oligomer (a1),
(a'') 39 to 56 wt.-%, in particular 42 to 47 wt.-%, polyfunctional monomer, wherein the polyfunctional monomer is preferably a mixture of UDMA, TEGDMA and bis-GMA,
(b) 0.5 to 2 wt.-%, particularly preferably 0.7 to 1.5 wt.-%, in particular 0.8 to 1.3 wt.-%, photoinitiator,
(a''') 0 to 15 wt.-%, particularly preferably 7 to 14 wt.-%, in particular 8 to 12 wt.-%, monofunctional monomer, wherein the monofunctional monomer (a) preferably comprises dicyclopentanyl methacrylate and/or p-cumylphenoxyethylene glycol methacrylate and in particular dicyclopentanyl methacrylate,
(c) 0.0001 to 2.0 wt.-%, particularly preferably 0.001 to 0.5 wt.-%, particularly preferably 0.01 to 0.1 wt.-%, UV absorber,
(d) 0.001 to 0.1 wt.-%, particularly preferably 0.002 to 0.05 wt.-%, optical brightener,
(e) 0 to 40 wt.-%, in particular 0 to 20 wt.-%, particularly preferably 0 wt.-%, filler and
(f) 0 to 3.0 wt.-%, in particular 0 to 2.0 wt.-%, particularly preferably 0 wt.-%, thixotropic additive,
in each case relative to the total weight of the composition, wherein the mixture of UDMA, TEGDMA and bis-GMA preferably comprises, relative to the total weight of the composition,
(a''1) 10 to 20 wt.-%, particularly preferably 12 to 16 wt.-%, UDMA,
(a''2) 20 to 35 wt.-%, particularly preferably 21 to 29 wt.-%, TEGDMA and
(a''3) 3 to 20 wt.-%, particularly preferably 3 to 10 wt.-%, bis-GMA.

In a further quite preferred embodiment the composition comprises:
(a') 37 to 55 wt.-%, in particular 38 to 44 wt.-%, such as e.g. 39 to 42 wt.-%, oligomer, preferably oligomer (a1),
(a'') 35 to 50 wt.-%, in particular 37 to 42 wt.-%, polyfunctional monomer, wherein the polyfunctional monomer is preferably a mixture of UDMA, TEGDMA and bis-GMA,
(b) 0.5 to 2 wt.-%, particularly preferably 0.7 to 1.5 wt.-%, in particular 0.8 to 1.3 wt.-%, photoinitiator,
(a''') 0 to 15 wt.-%, particularly preferably 7 to 14 wt.-%, in particular 8 to 12 wt.-%, monofunctional monomer, wherein the monofunctional monomer (a) preferably comprises dicyclopentanyl methacrylate and/or p-cumylphenoxyethylene glycol methacrylate and in particular dicyclopentanyl methacrylate,
(c) 0 to 2.0 wt.-%, particularly preferably 0.001 to 0.5 wt.-%, particularly preferably 0.01 to 0.1 wt.-%, UV absorber,
(d) 0.001 to 0.1 wt.-%, particularly preferably 0.002 to 0.05 wt.-%, optical brightener,
(e) 0 to 40 wt.-%, in particular 0 to 20 wt.-%, particularly preferably 7 to 15 wt.-% or 8 to 12 wt.-%, filler, wherein the filler is preferably a mixture of the above-described fillers (i), (ii) and (iii), and
(f) 0 to 3.0 wt.-%, in particular 0.1 to 2.0 wt.-%, particularly preferably 0.5 to 1.6 wt.-%, thixotropic additive, wherein the thixotropic additive is preferably $SiO_2$,
in each case relative to the total weight of the composition, wherein the mixture of UDMA, TEGDMA and bis-GMA preferably comprises, relative to the total weight of the composition,
(a''1) 10 to 20 wt.-%, particularly preferably 10 to 15 wt.-%, UDMA,
(a''2) 20 to 35 wt.-%, particularly preferably 21 to 26 wt.-%, TEGDMA and
(a''3) 3 to 20 wt.-%, particularly preferably 3 to 8 wt.-%, bis-GMA.

The rheological properties of the compositions according to the invention are matched to the desired intended use. Materials for stereolithographic processing are preferably adjusted such that their viscosity lies in the range of from 50 mPa·s to 100 Pa·s, preferably 100 mPa·s to 10 Pa·s, particularly preferably 100 mPa·s to 5 Pa·s. The viscosity is determined with a cone-plate viscometer at the desired processing temperature for the materials (shear rate 100/s). The processing temperature preferably lies in the range of from 10 to 70° C., particularly preferably 20 to 30° C. The composition according to the invention particularly preferably has a viscosity <10 Pa·s at 25° C. Because of the low viscosity, the composition according to the invention is suitable for being cured using additive manufacturing processes, such as e.g. 3D printing or stereolithography.

In addition, the composition according to the invention is characterized in that before and in particular even after the light curing it has a high transparency and little inherent colour.

In addition, the composition according to the invention is characterized in that the materials obtained after the curing have a high fracture toughness. Dental parts which are obtained by curing the composition according to the invention thus, to a high degree, withstand deformations without breaking. A cured part preferably has an outer fibre strain of more than 7%, in particular an outer fibre strain of more than 10%, particularly preferably an outer fibre strain of more than 11%, such as e.g. an outer fibre strain of 12%. The outer-fibre strain is determined in a three-point flexural test according to ISO 4049 with a support span of 20 mm, wherein a length sensor is arranged on the underside of the test piece in order to determine the exact bending on the underside of the sample piece. The outer fibre strain in percent ($\varepsilon_f$) is calculated using the formula $\varepsilon_f = (600 \cdot s1 \cdot h)/L^2$, wherein s1 is the bending at break of the test piece, measured on the underside of the test piece, h is the height of the test piece and L is the support span. After the curing the composition according to the invention particularly preferably has such an outer-fibre strain that test pieces do not break during a flexural test according to ISO 4049 with a support span of 20 mm at a bending of 4 mm.

Moreover, the composition according to the invention is characterized in that the materials obtained after the curing have a high flexural strength and a high flexural modulus. Dental parts which are obtained by curing the composition according to the invention thus have a high stiffness and oppose a deformation with a high level of resistance. A cured dental part preferably has a flexural strength, determined according to ISO 4049, of from 40 to 140 MPa, in particular a flexural strength of 50 MPa or more, such as e.g. 50 to 80 MPa, particularly preferably a flexural strength of more than 55 MPa. Furthermore, a cured part preferably has a flexural modulus, determined according to ISO 4049, of from 800 to 3800 MPa, such as 1000 to 2500 MPa, in particular a flexural modulus of more than 1000 MPa, particularly preferably a flexural modulus of more than 1200 MPa or more than 1300 or more than 1500 or more than 1800 MPa.

In addition, the composition according to the invention is characterized in that the materials obtained after the curing have a high fracture toughness and a high fracture work. A dental part which is obtainable by curing the composition according to the invention preferably has a fracture toughness $K_{max}$ of from 0.5 to 1.8 MPa·m$^{1/2}$, in particular of at least 0.6 MPa·m$^{1/2}$, particularly preferably at least 0.8 MPa·m$^{1/2}$ or at least 1.0 MPa·m$^{1/2}$ or at least 1.2 MPa·m$^{1/2}$, and/or a fracture work FW of from 70 to 600 J/m$^2$, such as e.g. 100 to 450 J/m$^2$, in particular of at least 110 J/m$^2$, particularly preferably at least 150 J/m$^2$ or at least 180 J/m$^2$ or at least 250 J/m$^2$, wherein the fracture toughness $K_{max}$ and the fracture work FW are determined according to the test method described below.

Because of the above properties, compositions according to the invention are outstandingly suitable as dental material and in particular for the production or repair of dental parts. The present invention therefore also relates to the use of a composition according to the invention as dental material and in particular for the production or repair of dental parts, such as e.g. dental restorations, prostheses, prosthesis materials, artificial teeth, inlays, onlays, crowns, bridges, drilling templates, try-ins or orthodontic appliances. The composition according to the invention is particularly preferably suitable for the production of orthodontic appliances, in particular aligners, positioners, aligner attachments, positioners bearing aligner attachments, occlusal splints, transfer splints or orthodontic splints.

The present invention therefore also relates to a process for the production of dental parts, in particular for the production of the above-named dental parts, in which a composition according to the invention is cured with the aid of light in order to yield the dental part. Furthermore, the invention also relates to dental parts, in particular the above-named parts, which are obtainable through such a process.

The production or repair of dental parts is effected in particular extraorally. In addition, it is preferred that the production or repair of dental parts is effected through an additive process, in particular using 3D printing or a lithography-based process, such as e.g. stereolithography.

The production of the dental part according to the invention is preferably effected through a stereolithographic process. For this purpose, a virtual copy of the tooth situation is created by direct or indirect digitization of the tooth to be restored or of the teeth to be restored on a computer, then a model of the dental restoration is constructed on the computer on the basis of this copy and this model is then produced by additive stereolithographic manufacturing. The production of an orthodontic appliance using a stereolithographic process is carried out correspondingly. Once a virtual model of the orthodontic appliance to be produced has been created, the composition according to the invention is polymerized by selective light irradiation. The geometry of the orthodontic appliance can be constructed in layers by polymerizing a plurality of thin layers with the desired cross section one after another. The layered construction of the geometry is usually followed by a cleaning of the dental part by treatment with a suitable solvent, such as e.g. an alcohol, such as ethanol or isopropanol, a ketone, a ketal or an ester, and a post-treatment by irradiation of the part with a suitable wavelength, such as e.g. an irradiation with an intensity of 25 mW/cm$^2$ at 405 nm and at the same time 130 mW at 406 nm for 15 min, in which the part is irradiated with light of a suitable wavelength in order to further reduce the residual monomer content and improve the mechanical properties.

The invention is explained in more detail in the following with reference to embodiment examples.

EMBODIMENT EXAMPLES

Examples 1 to 14

The components listed in Tables 1 to 2 were mixed homogeneously with each other in the quantities indicated. For this purpose, except for the glass fillers and prepolymer fillers, all solid components were dissolved in the monomers, accompanied by stirring, for approximately 60 min in a stirring unit with dissolver disc. The oligomer was then added and it was stirred until a homogeneous mixture was achieved (approximately 60 min). Unfilled compositions (see Examples 1 to 7 and 11) were then ready for use. For the case where the composition contains a filler (see Examples 8 to 10 and 12 to 14), this was then stirred in with the aid of the stirring unit within 15 min, then milled twice by means of a rotary milling machine and then stirred again for 15 min.

TABLE 1

Compositions for the production of e.g. splints or drilling templates

| Component | Composition [wt.-%] | | | | | |
| --- | --- | --- | --- | --- | --- | --- |
| | 1 | 2 | 3 | 4 | 5 | 6 |
| TEGDMA[1] | 23.0 | 23.0 | 23.0 | 23.0 | 23.0 | 29.0 |
| UDMA[2] | 18.0 | 18.0 | 18.0 | 18.0 | 18.0 | 15.0 |
| bis-GMA[3] | 18.0 | 18.0 | 18.0 | 18.0 | 18.0 | 5.0 |
| Oligomer (a1)[4] | — | — | — | — | 40.0 | 50.0 |
| Oligomer (a3)[5] | 40.0 | — | — | — | — | — |
| Oligomer (a5)[6] | — | 40.0 | — | — | — | — |
| Oligomer (a4)[7] | — | — | 40.0 | — | — | — |
| Oligomer (a3)[8] | — | — | — | 40.0 | — | — |
| TPO[9] | 0.85 | 0.85 | 0.85 | 0.85 | 0.85 | 0.85 |
| Bumetrizole | 0.15 | 0.15 | 0.15 | 0.15 | 0.15 | 0.15 |
| Viscosity (23° C.) oscill. [MPa*s] | 4.8 | 1.3 | 5.2 | — | 5.6 | 3.2 |
| Kmax [MPa m$^{1/2}$] wet | 0.8 | 0.8 | 0.8 | 0.9 | 1.2 | — |
| FW [J/m$^2$] wet | 147 | 114 | 99 | 169 | 189 | — |

[1]Triethylene glycol dimethacrylate (CAS No. 109-16-0)
[2]Urethane dimethacrylate (CAS No. 72869-86-4)
[3]Addition product of methacrylic acid and bisphenol A diglycidyl ether
[4]Oligomer (a1) with R$^9$ and R$^{10}$ = H and a molar mass of approx. 2200 g/mol
[5]Oligomer (a3) with R$^9$ and R$^{10}$ = CH$_3$
[6]Oligomer (a5) with R$^9$ and R$^{10}$ = CH$_3$
[7]Oligomer (a4) with R$^9$ and R$^{10}$ = CH$_3$
[5]Oligomer (a3) with R$^9$ and R$^{10}$ = H
[9]Diphenyl(2,4,6-trimethylbenzoyl)phenylphosphine oxide (CAS No. 75980-60-8)

TABLE 2

Compositions for the production of e.g. positioners bearing aligner attachments

| Component | Composition [wt.-%] | | | | | | | |
|---|---|---|---|---|---|---|---|---|
| | 7 | 8 | 9 | 10 | 11 | 12 | 13 | 14 |
| TEGDMA[1] | 25.70 | 23.26 | 20.82 | 18.39 | 25.70 | 23.26 | 20.82 | 18.39 |
| UDMA[2] | 13.27 | 12.01 | 10.75 | 9.49 | 13.27 | 12.01 | 10.75 | 9.49 |
| bis-GMA[3] | 5.00 | 4.53 | 4.05 | 3.58 | 5.00 | 4.53 | 4.05 | 3.58 |
| Glycerol 1,3-dimethacrylate-2-acetate[4] | 10.00 | 9.05 | 8.10 | 7.15 | — | — | — | — |
| Dicyclopentanyl methacrylate[5] | — | — | — | — | 10.00 | 9.05 | 8.10 | 7.15 |
| Oligomer (a1)[6] | 45.00 | 40.73 | 36.46 | 32.20 | 45.00 | 40.73 | 36.46 | 32.20 |
| TPO[7] | 1.00 | 0.91 | 0.81 | 0.72 | 1.00 | 0.91 | 0.81 | 0.72 |
| Bumetrizole | 0.03 | 0.02 | 0.02 | 0.02 | 0.03 | 0.02 | 0.02 | 0.02 |
| Glass filler[8] | — | 4.45 | 8.90 | 13.34 | — | 4.45 | 8.90 | 13.34 |
| Prepolymer filler[9] | — | 5.04 | 10.09 | 15.11 | — | 5.04 | 10.09 | 15.11 |
| Viscosity (23° C.) oscill. [MPa*s] | ~2.0 | 2.0 | 2.9 | 5.0 | 2.0 | 2.1 | 3.1 | 7.0 |
| Flexural strength [MPa] dry | 89 | 94 | 98 | 104 | 70 | 80 | 95 | 96 |
| Flexural modulus [MPa] dry | 2042 | 2312 | 2655 | 2994 | 1532 | 1957 | 2500 | 2644 |
| Outer-fibre strain at break [%] dry | 9.6 | 8.1 | 7.0 | 7.2 | n.b. | n.b. | 11.7 | 9.2 |
| Flexural strength [MPa] wet | 70 | 67 | 72 | 76 | 59 | 59 | 75 | 79 |
| Flexural modulus [MPa] wet | 1621 | 1535 | 1886 | 2037 | 1285 | 1462 | 2043 | 2156 |
| Outer-fibre strain at break [%] wet | 9.8 | 7.2 | 7.8 | 7.5 | n.b. | n.b. | 10.0 | 9.1 |
| Kmax [MPa m$^{1/2}$] dry | 1.2 | 1.0 | 1.3 | 1.3 | 1.2 | — | — | 1.2 |
| FW [J/m$^2$] dry | 156 | 97 | 161 | 150 | 173 | — | — | 128 |
| Kmax [MPa m$^{1/2}$] wet | 1.1 | 1.1 | 1.1 | 1.3 | 1.4 | 1.3 | 1.2 | 1.2 |
| FW [J/m$^2$] wet | 189 | 170 | 157 | 206 | 383 | 282 | 182 | 163 |

[1] Triethylene glycol dimethacrylate (CAS No. 109-16-0)
[2] Urethane dimethacrylate (CAS No. 72869-86-4)
[3] Addition product of methacrylic acid and bisphenol A diglycidyl ether
[4] CAS No. 1360927-06-5
[5] CAS No. 34759-34-7
[6] Oligomer (a1) with $R^9$ and $R^{10}$ = H and a molar mass of approx. 2200 g/mol
[7] Diphenyl(2,4,6-trimethylbenzoyl)phenylphosphine oxide (CAS No. 75980-60-8)
[8] Mixture of a silanized glass filler with a particle size of approximately 0.7 μm (before the silanization) and a silanized glass filler with a particle size of approximately 1.0 μm (before the silanization) in a ratio by weight of approximately 2:1
[9] Prepolymer filler (so-called isofiller, i.e. a ground composite material) with a particle-size distribution of from approximately 0.1 to approximately 10 μm
n.b.: Test piece not broken The compositions of Examples 1 to 14 were used for the additive manufacture of three-dimensional components in a stereolithographic process. For this purpose, test pieces were produced by means of a stereolithography printer in the bottom-up process. The printer exposed the samples to light using the DLP technique with a wavelength of 388 nm, a power of 10 mW/cm$^2$ and a pixel size of 50 μm in a layered construction. The layer thickness was 50 μm in each case.

The test pieces produced in this way had a dimension of 50 mm in length, 4 mm in thickness and 8 mm in height, wherein the test pieces, including a notch with a depth of 3 mm, in the middle in each case, were printed out on the upper side of the test piece. The notch was 1 mm wide in each case and extended over the entire thickness of the test piece (4 mm).

After being printed out, the test pieces were cleaned and post-treated. Then, by means of a razor blade, a perpendicular cut with a depth of approx. 300 μm was made precisely in the middle of the notch in each case and the test pieces were stored in mains water ("wet") or in air ("dry") for 24 h at 37° C.

The determination of the outer fibre strain, the flexural strength and the flexural modulus was effected using the above-described process according to ISO 4049.

The determination of the fracture toughness $K_{max}$ and the fracture work FW was effected in accordance with ISO 20795-1:2013 in the 3-point flexural test with a support span of 32 mm. The determination of $K_{max}$ and FW is based on the theoretical principles of the stress intensity factor $K_{Ic}$.

The fracture toughness $K_{max}$ is the highest factor of the load intensity, or also called the stress intensity factor at highest load, and is calculated as follows:

$$K_{max} = \left(\frac{P_{max} \cdot S}{B \cdot W^{\frac{3}{2}}}\right) \cdot f(x) \cdot 0.031 \; MPa \cdot m^{1/2}, \text{ with}$$

$$f(x) = 3 \cdot \sqrt{x} \, \frac{1.99 - x(1-x) \cdot (2.15 - 3.93x + 2.7x^2)}{2(1+2x) \cdot (1-x)^{\frac{3}{2}}},$$

$$\text{wherein } x = \frac{a}{W}$$

and W is the sample piece height (=8 mm), B is the sample piece thickness (=4 mm), a is the tear length (=3 mm+tear depth with razor blade, S is the support span (=32 mm) and $P_{max}$ is the maximum pressure in the test.

The calculation of the fracture work (total fracture work) was effected as follows:

$$FW = \frac{U}{2B(W-a)} \cdot 1000 \; J/m^2$$

wherein U is the total energy which is required to break the sample (integral of the load/displacement graph) and which is needed to create the two new fracture planes B(W−a). This parameter describes the resistance of the material to the crack propagation and is dependent on the sample dimensions and the test conditions.

The test pieces displayed no visually perceptible inherent colour, but rather were colourless and highly transparent.

The invention claimed is:
1. Polymerizable composition comprising
    (a) at least one radically polymerizable compound,
    (b) at least one initiator for the radical polymerization,
    (c) at least one UV absorber and
    (d) at least one optical brightener,
    and wherein the composition comprises
        from 25 to 60 wt.-% of at least one radically polymerizable oligomer, from 30 to 65 wt.-% of at least one radically polymerizable, polyfunctional monomer and from 0 to 15 wt.-% of one or more radically polymerizable, monofunctional monomers as the at least one radically polymerizable compound (a),
        from 0.1 to 3.0 wt.-% of at least one photoinitiator as the initiator (b),
        from 0.0001 to 2.0 wt.-% of the at least one UV absorber (c),
        from 0.001 to 0.1 wt.-% of the at least one optical brightener (d),
        from 0 to 40 wt.-% filler (e) and
        from 0 to 3.0 wt.-% thixotropic additive (f),
        in each case relative to the total weight of the composition.

2. Polymerizable composition according to claim 1, wherein the at least one optical brightener (d) is a fluorescent compound and is a compound which absorbs light with a wavelength of less than 400 nm and emits light with a wavelength of from approximately 400 to 450 nm.

3. Polymerizable composition according to claim 1, wherein the at least one optical brightener (d) is selected from the group consisting of 2,5-bis(5-tert-butyl-benzoxazol-2-yl)thiophene, terephthalic acid derivatives and mixtures thereof.

4. Polymerizable composition according to claim 1, wherein at least one UV absorber (c) is selected from the group consisting of azo dyes, carbonyl dyes, cyanine dyes, azomethines, methines, phthalocyanines, dioxazines, benzotriazoles, benzophenones, triazines, amine stabilizers and mixtures thereof.

5. Polymerizable composition according to claim 4,
    wherein the at least one UV absorber (c) is selected from the group consisting of 2,2'-methylenebis[6-(2H-benzotriazol-2-yl)-4-(1,1,3,3-tetramethylbutyl)phenol], 2,2',4,4'-tetrahydroxybenzophenone, 2-tert-butyl-6-(5-chloro-2H-benzotriazol-2-yl)-4-methylphenol, 2,2'-benzene-1,4-diylbis(4h-3,1-benzoxazin-4-one), 2-(4,6-bis-(2,4-dimethylphenyl)-1,3,5-triazin-2-yl)-5-(octyloxy)phenol, 2-(2-hydroxy-5-methylphenyl) benzotriazole, 2-(2-hydroxyphenyl)benzotriazole, 2-(2H-benzotriazol-2-yl)-6-dodecyl-4-methylphenol, 2-(2'-hydroxy-3',5'-di-t -butylphenyl)-5-chlorobenzotriazole, 2,2'-dihydroxy-4-methoxybenzophenone, 2,2'-dihydroxy-4,4'-dimethoxybenzophenone, bis(1,2,2,6,6-pentamethyl-4-piperidyl) sebacate, methyl-1,2,2,6,6-pentamethyl-4-piperidyl sebacate, bis(1-octyloxy-2,2,6,6-tetramethyl-4-piperidyl) sebacate and bis(1,2,2,6,6-pentamethyl-4-piperidyl) [[3,5-bis(1,1-dimethylethyl)-4-hydroxyphenyl]methyl] butylmalonate and mixtures thereof.

6. Polymerizable composition according to claim 4,
    wherein the at least one UV absorber (c) is 2-tert-butyl-6-(5-chloro-2H-benzotriazol-2-yl)-4-methylphenol or 2,2',4,4'-tetrahydroxybenzophenone.

7. Polymerizable composition according to claim 1,
    wherein the at least one UV absorber (c), relative to the total weight of the composition, is present in an amount of from 0.0001 to 2.0 wt.-%,
    wherein the composition comprises 2-tert-butyl-6-(5-chloro -2H-benzotriazol-2-yl)-4-methylphenol in an amount of from 0.01 to 0.2 wt.-%, or 2,2',4,4'-tetrahydroxybenzophenone in an amount of from 0.01 to 0.07 wt.-% as the at least one UV absorber (c).

8. Polymerizable composition according to claim 1,
    wherein the ratio by weight of the at least one UV absorber (c) to the at least one optical brightener (d) is from 2:1 to 50:1 or from 10:1 to 25:1.

9. Polymerizable composition according to claim 1,
    wherein the oligomer is selected from the group consisting of aliphatic urethane (meth)acrylate oligomers, epoxy (meth)acrylate oligomers, polyether urethane (meth)acrylate oligomers and mixtures thereof, or
    wherein the oligomer is selected from the group consisting of (a1) an oligomer which is obtainable by polymerization of 2-hydroxyethyl (meth) acrylate, 1-isocyanato-3-isocyanatomethyl-3,5,5-trimethylcyclohexane, ε-caprolactone and 2-(2-hydroxyethoxy)ethanol, (a2) an oligomer which is obtainable by polymerization of 2-hydroxyethyl (meth)acrylate, 1-isocyanato-3-isocyanatomethyl-3,5, 5-trimethylcyclohexane, adipic acid and ethylene glycol, (a3) an oligomer which is obtainable by polymerization of 2-hydroxyethyl (meth) acrylate, 1-isocyanato-3-isocyanatomethyl-3,5,5-trimethylcyclohexane and tetrahydrofuran, (a4) an oligomer which is obtainable by polymerization of 2-hydroxyethyl (meth)acrylate, 1-isocyanato-3-isocyanatomethyl-3,5,5-trimethylcyclohexane and ethylene glycol, (a5) an oligomer which is obtainable by polymerization of 2-hydroxyethyl (meth)acrylate, 2,2,4-trimethylhexanediol diisocyanate and ethylene glycol, (a6) an oligomer which is obtainable by polymerization of 2-hydroxyethyl (meth)acrylate, 2,2,4-trimethylhexanediol diisocyanate and tetrahydrofuran, and mixtures thereof.

10. Polymerizable composition according to claim 9 comprising an oligomer (a1) as the at least one radically polymerizable oligomer,
    wherein the oligomer (a1) is an oligomer of structural formula (I)

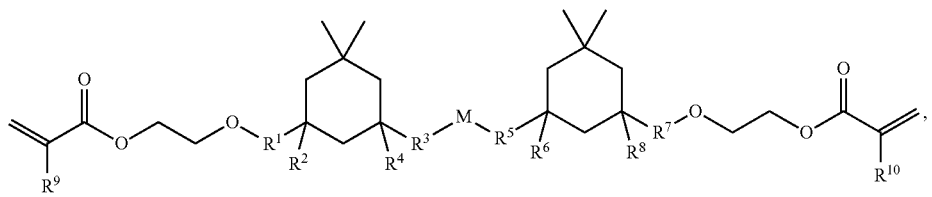
(I)

in which
R¹ and R⁵ each are —C(=O)—NH— or —C(=O)—NH—CH₂—,
R³ and R⁷ each are —NH—C(=O)— or CH₂—NH—C(=O)—,
R², R⁴, R⁶ and R⁸ each are H or CH₃,
R⁹ and R¹⁰ each are H or CH₃,
wherein,
if R¹ is —C(=O)—NH—, then R² is H, R³ is —CH₂—NH—C(=O)— and R⁴ is CH₃ and,
if R¹ is —C(=O)—NH—CH₂—, then R² is CH₃, R³ is —NH—C(=O)— and R⁴ is H, and M is a mid-chain segment which is obtainable by polymerization of ε-caprolactone and 2-(2-hydroxyethoxy)ethanol or by polymerization of 1-isocyanato-3-isocyanatomethyl-3,5,5-trimethylcyclohexane, ε-caprolactone and 2-(2-hydroxyethoxy)ethanol, or wherein the oligomer (a1) is an oligomer of structural formula (II)

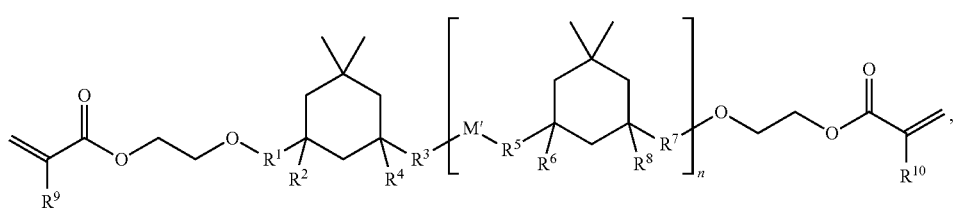
(II)

in which
M' is a mid-chain segment which is obtainable by polymerization of ε-caprolactone and 2-(2-hydroxyethoxy)ethanol, and
n is a whole number from 1 to 10, or
wherein the mid-chain segment M' of Formula (II) is described by structural formula (III)

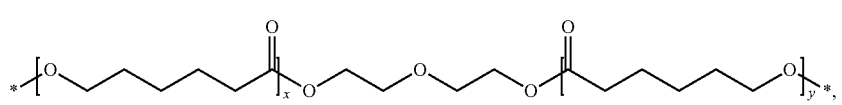
(III)

in which
x is a number from 1 to 20, and
y is a number from 1 to 20.

11. Polymerizable composition according to claim 1, wherein the polyfunctional monomer is selected from the group consisting of di- and trifunctional acrylates and polyfunctional methacrylates with a molecular weight of <1000 g/mol and mixtures thereof.

12. Polymerizable composition according to claim 1, wherein the polyfunctional monomer is selected from the group consisting of glycerol 1,3-dimethacrylate-2-acetate, aliphatic urethane diacrylates, phthalic acid di-2-hydroxyethylacrylate ester, pyromellitic acid di-di-2-hydroxyethylacrylate ester, bis-G(M)A, 2,2-bis[4-(2-(meth)acryloxypropoxy)phenyl]propane, urethane di(meth)acrylate, triethylene glycol di(meth)acrylate, tricyclodecane dimethanol dimethacrylate, and the reaction product of 1,3-phenylenebis(propane-2,2-diylcarbamoyloxyethane-2,1-diyl) bis(2-methylacrylate), 2-{[(2-{-[2-methacryloyloxy)ethoxy]carbonyl}amino)propan-2-yl]phenyl}propan-2-yl)carbamoyl]oxy}propyl methacrylate and 1,3-phenylenebis(propane-2,2-moyloxypropane-2,1-diyl) bis(2-methylacrylate) as well as mixtures thereof.

13. Polymerizable composition according to claim 1, wherein the at least one initiator (b) is selected from the group consisting of camphorquinone, ethyl 4-(dimethylamino)benzoate, phenylbis(2,4, 6-trimethylbenzoyl) phosphine oxide, diphenyl(2,4, 6-trimethylbenzoyl) phenylphosphine oxide, 2-benzyl-2-(dimethylamino)-4'-morpholinobutyrophenone, 1-butanone-2-(dimethylamino)-2-(4-methylphenyl)methyl-1-4-(4-morpholinyl)phenyl, acylgermanium compounds and combinations thereof, or is selected from the group consisting of phenylbis(2,4, 6-trimethylbenzoyl) phosphine oxide, diphenyl(2,4, 6-trimethylbenzoyl)phenylphosphine oxide, bis(4-methoxybenzoyl)diethylgermanium, tetrakis(4-ethoxybenzoyl)germanium, tetrakis(4-propoxybenzoyl)germanium and combinations thereof.

14. Polymerizable composition according to claim 1,
wherein the monofunctional monomer is selected from the group consisting of dicyclopentanyl methacrylate, p-cumylphenoxyethylene glycol methacrylate and mixtures thereof.

15. Polymerizable composition according to claim 1, comprising
up to 15 vol.-% of the filler (e).

16. Process for the production or repair of a dental part, wherein a composition according to claim 1 is cured with the aid of light in order to yield the dental part.

17. Process according to claim 16,
wherein the dental part is a dental restoration, a prosthesis, a prosthesis material, an artificial tooth, an inlay, an onlay, a crown, a bridge, a drilling template, a try-in or an orthodontic appliance, an aligner, a positioner, an aligner attachment, a positioner bearing an aligner attachment, an occlusal splint, a transfer splint and/or an orthodontic splint.

18. Process according to claim 16,
wherein the production or repair of dental parts is effected through an additive process using 3D printing or a lithography-based process.

* * * * *